US012564626B2

(12) United States Patent
Koumans et al.

(10) Patent No.: US 12,564,626 B2
(45) Date of Patent: Mar. 3, 2026

(54) SERUM FREE INTRACELLULAR PATHOGEN VACCINE

(71) Applicant: Intervet Inc., Madison, NJ (US)

(72) Inventors: Joseph Koumans, Wageningen (NL); Petter Frost, Radal (NO); Maria Forlenza, Wageningen (NL)

(73) Assignee: Intervet Inc., Rahway, NJ (US)

( * ) Notice: Subject to any disclaimer, the term of this patent is extended or adjusted under 35 U.S.C. 154(b) by 1041 days.

(21) Appl. No.: 17/414,156

(22) PCT Filed: Dec. 20, 2019

(86) PCT No.: PCT/EP2019/086630
§ 371 (c)(1),
(2) Date: Jun. 15, 2021

(87) PCT Pub. No.: WO2020/127941
PCT Pub. Date: Jun. 25, 2020

(65) Prior Publication Data
US 2022/0080040 A1 Mar. 17, 2022

(30) Foreign Application Priority Data
Dec. 21, 2018 (EP) ...................................... 18215363

(51) Int. Cl.
| | |
|---|---|
| *A61K 39/205* | (2006.01) |
| *A23K 10/16* | (2016.01) |
| *A23K 10/18* | (2016.01) |
| *A23K 10/24* | (2016.01) |
| *A23K 20/147* | (2016.01) |
| *A23K 50/80* | (2016.01) |
| *A61K 35/16* | (2015.01) |
| *A61K 39/002* | (2006.01) |
| *A61K 39/005* | (2006.01) |
| *A61K 39/02* | (2006.01) |
| *A61K 39/12* | (2006.01) |
| *A61K 39/145* | (2006.01) |
| *A61P 31/12* | (2006.01) |
| *A61K 39/00* | (2006.01) |

(52) U.S. Cl.
CPC ............ *A61K 39/205* (2013.01); *A23K 10/16* (2016.05); *A23K 10/18* (2016.05); *A23K 10/24* (2016.05); *A23K 20/147* (2016.05); *A23K 50/80* (2016.05); *A61K 35/16* (2013.01); *A61K 39/002* (2013.01); *A61K 39/005* (2013.01); *A61K 39/0208* (2013.01); *A61K 39/0233* (2013.01); *A61K 39/12* (2013.01); *A61K 39/145* (2013.01); *A61P 31/12* (2018.01); *A61K 2039/552* (2013.01); *A61K 2039/70* (2013.01)

(58) Field of Classification Search
CPC ...... A61K 2039/521; A61K 2039/5252; A61K 2039/552; A61K 39/02; A61K 39/0208; A61K 39/0233; A61K 39/12; A61K 2039/5254; A61K 2039/70; A61K 39/155; A61K 39/17; A61K 39/295; A61K 39/165; C12N 2720/10034; C12N 15/86; C12N 2760/18171; C12N 2760/18571; C12N 2760/18134; C12N 2760/18122; A61P 31/14; A61P 31/12; A23K 50/80; Y02A 40/81
See application file for complete search history.

(56) References Cited

U.S. PATENT DOCUMENTS

| | | | |
|---|---|---|---|
| 665,671 A | 1/1901 | Chapman | |
| 5,753,489 A | 5/1998 | Kistner et al. | |
| 6,825,036 B2 | 11/2004 | Makizumi et al. | |
| 9,441,207 B2 | 9/2016 | Warthen et al. | |

FOREIGN PATENT DOCUMENTS

| | | | | | |
|---|---|---|---|---|---|
| CA | 3037337 A1 | * | 9/2017 | ............. | A61K 39/12 |
| CA | 3050136 A1 | * | 1/2018 | ............. | A61K 39/12 |
| JP | 2003219873 A | | 8/2003 | | |
| KR | 10-2016-0074818 A | | 6/2016 | | |
| KR | 20160074818 A | | 6/2016 | | |
| RU | 2092185 C1 | | 10/1997 | | |
| RU | 2183972 C2 | | 6/2002 | | |
| RU | 2287582 C2 | | 11/2006 | | |
| RU | 2369635 C2 | | 10/2009 | | |
| RU | 2015145113 A | | 4/2017 | | |
| RU | 2624862 C2 | | 7/2017 | | |

(Continued)

OTHER PUBLICATIONS

Haugland et al. J. Virol. 2011, vol. 85 (11), pp. 5275-5286.*
Aunsmo, A., Association of spinal deformity and vaccine-induced abdominal lesions in harvest-sized Atlantic salmon, *Salmo salar* L., Journal of Fish Diseases, 2008, 515-524, vol. 31, No. 7.

(Continued)

*Primary Examiner* — Bao Q Li

(74) *Attorney, Agent, or Firm* — Susanna C. Benn

(57) ABSTRACT

A vaccine composition comprising a virus antigen wherein the composition comprises less than 5% serum, wherein the virus antigen is a whole virus or derived from a whole virus, the vaccine composition reduces, prevents or avoids cross-stitch spinal deformity in the treated animal. Said vaccine composition for use in a method of treating a disease caused by the intracellular pathogen in an animal and reducing, preventing or avoiding cross-stitch spinal deformity in the treated animal. In cross-stitch vertebra the intervertebral space is completely collapsed. A vaccine composition for use as defined above wherein the animal is a fish. In an embodiment the pathogen is salmon alpha virus (SAV).

12 Claims, 5 Drawing Sheets

(56) References Cited

FOREIGN PATENT DOCUMENTS

Figure 1:
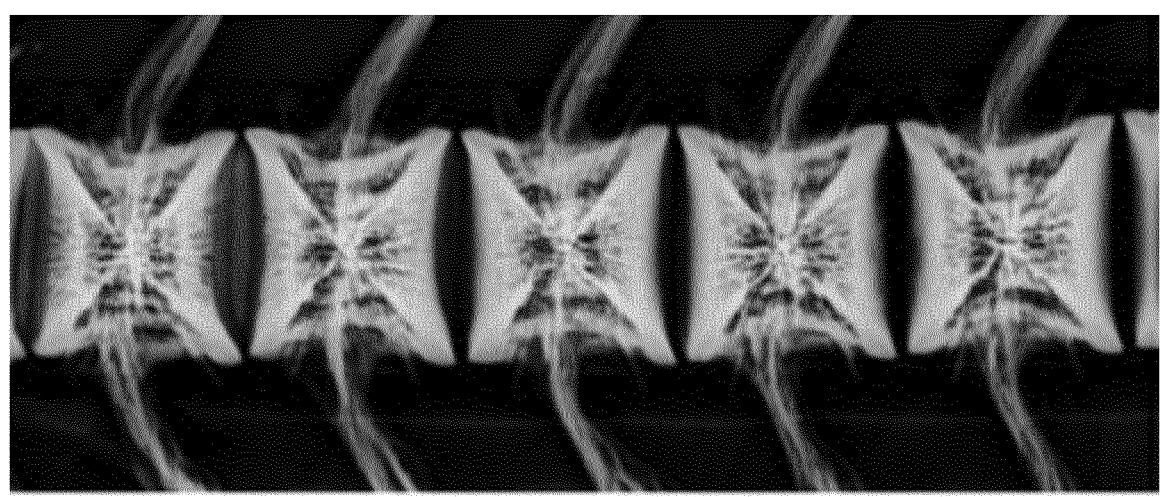
Figure 1:
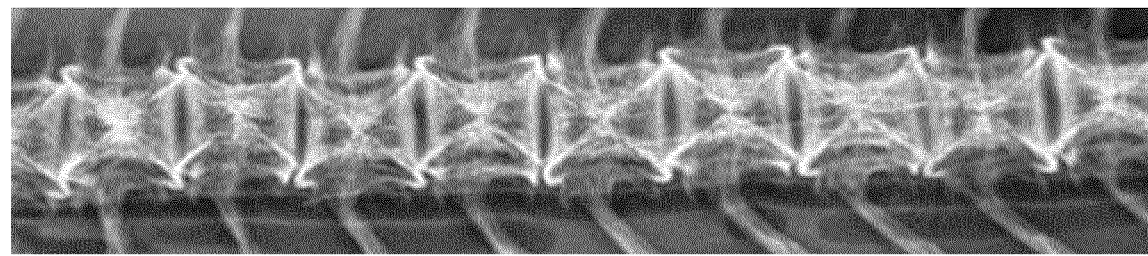

| RU | 2643929 C2 | 2/2018 |
|----|------------|--------|
| WO | WO 2001064846 A1 | 9/2001 |
| WO | 2004061093 A1 | 7/2004 |
| WO | 2007031572 A1 | 3/2007 |
| WO | 2013160913 A1 | 10/2013 |
| WO | WO 2017054100 A1 | 4/2017 |
| WO | 1999057246 A1 | 5/2019 |
| WO | 2020127941 A2 | 6/2020 |

OTHER PUBLICATIONS

Ballesteros, Natalia A., Oral immunization of rainbow trout to infectious pancreatic necrosis virus (lpnv) induces different immune gene expression profiles in head kidney and pyloric ceca, Fish and Shellfish Immunology, 2012, 174-185, vol. 33, No. 2.

Berg, Arne et al., Time of vaccination influences development of adhesions, growth and spinal deformities in Atlantic salmon *Salmo salar*, Diseases of Aquatic Organisms, 2006, 239-248, 69.

English Machine Translation for JP2003219873A, as downloaded from Google Patents on Dec. 19, 2019, 8 pages.

Fjelldal, Per Gunnar et al., A radiological study on the development of vertebral deformities in cultured Atlantic salmon (*Salmo salar* L.), Aquaculture, 2007, 721-728, 273.

Hu, Alan Yung-Chih, Production of Inactivated Influenza H5N1 Vaccines from MDCK Cells in Serum-Free Medium, Plos One, 2011, e14578, vol. 6, No. 1.

Karasawa, H., et al., Development of a suspension culture of chinook salmon (*Oncorhynchus tshawytscha*) embryo (CHSE-214) cells in a spinner flask, Bull. Eur. Ass. Fish Pathol., 1991, pp. 142-144, 11(4).

Lidgerding, B.C., Cell Lines for the production of viral fish disease agents, Develop. biol. Standard., 1981, pp. 233-241, 49.

Machine translation of WO2017054100, dated Jul. 18, 2019, 9 pages.

Rivas-Aravena, Andrea, Development of a nanoparticle-based oral vaccine for Atlantic salmon against ISAV using an alphavirus replicon as adjuvant, Fish and Shellfish Immunology, 2015, 157-166, vol. 45, No. 1.

Satoh, Minoru et al., Polyclonal hypergammaglobulinemia and autoantibody production induced by vaccination in farmed Atlantic salmon, Fish & Shellfish Immunology, 2011, 1080-1086, 30.

Shea, T.B. and Berry, E.S., A serum-free medium that supports the growth of piscine cell cultures, In Vitro, Nov. 1983, pp. 818-824, vol. 19, No. 11.

Silverstone, Andrew M. et al., Spinal deformities in farmed Atlantic salmon, Can. Vet. J., 2002, 782-784, 43.

Witten, P. Eckhard et al., Towards a classification and an understanding of developmental relationships of vertebral body malformations in Atlantic salmon (*Salmo salar* L.), Aquaculture, 2009, 6-14, 295.

Alphaject LiVac® SRS, Injectable vaccines; link: https://pharmaq.com/es/pharmaq/nuestros-productos/ (4 pages).

Dixon, P. F. et al., Inactivation of infectious pancreatic necrosis virus for vaccine use, Journal of Fish Diseases, 6 (5), 399-409, 1983.

Maisey, Kevin et al., Vaccines for piscirickettsiosis (salmonid rickettsial septicaemia, SRS): the Chile perspective, Expert Review of Vaccines, 16:3, 215-228, 2017.

Rodríguez-Tovar, Luis E. et al., Induction time for resistance to microsporidial gill disease caused by Loma salmonae following vaccination of rainbow trout (*Oncorhynchus mykiss*) with a spore-based vaccine, Fish & Shellfish Immunology, 21, 170-175, 2006.

Speare, D. J. et al., Development of an Effective Whole-Spore Vaccine to Protect against Microsporidial Gill Disease in Rainbow Trout (*Oncorhynchus mykiss*) by Using a Low-Virulence Strain of Loma salmonae, Clinical and Vaccine Immunology, 14(12), 1652-1654, 2007.

Wilhelm, Vivian et al., A vaccine against the salmonid pathogen Piscirickettsia salmonis based on recombinant proteins, Vaccine, 24, 5083-5091, 2006.

"With an international seminary, Pharmaq will introduce the first attenuated live vaccine against SRS", Published on: Mar. 28, 2016; Link: https://www.aqua.cl/2016/03/28/con-seminariointernacional-pharmaq-presentara-la-primera-vacuna-viva-atenuada-contra-srs/ (2 pages).

* cited by examiner

A

B

Fig. 2

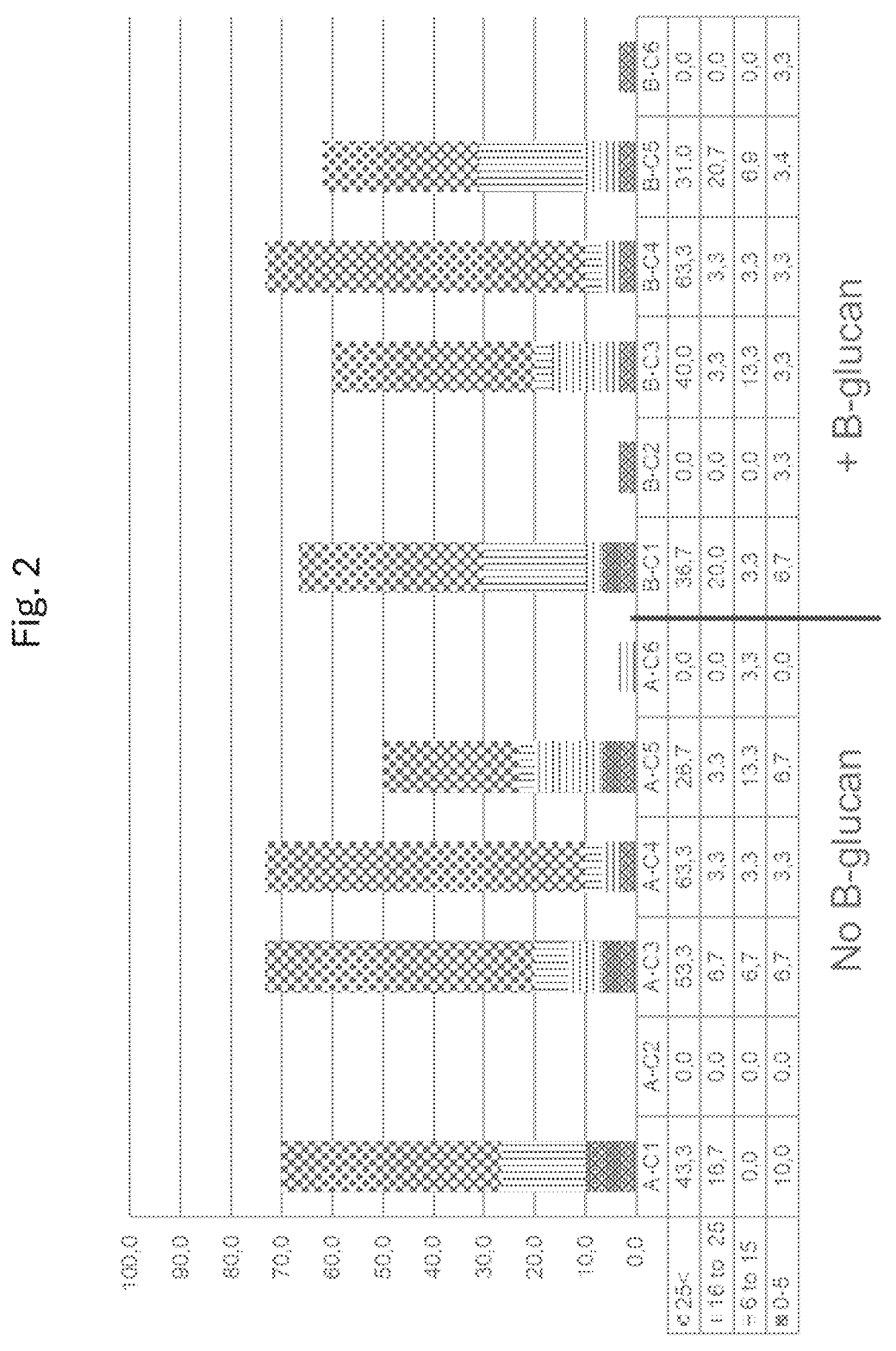

| | A-C1 | A-C2 | A-C3 | A-C4 | A-C5 | A-C6 | B-C1 | B-C2 | B-C3 | B-C4 | B-C5 | B-C6 |
|---|---|---|---|---|---|---|---|---|---|---|---|---|
| ≥ 25 | 43.3 | 0.0 | 63.3 | 63.3 | 26.7 | 0.0 | 36.7 | 0.0 | 40.0 | 63.3 | 31.0 | 0.0 |
| 16 to 25 | 10.7 | 0.0 | 6.7 | 3.3 | 3.3 | 0.0 | 20.0 | 0.0 | 3.3 | 3.3 | 20.7 | 0.0 |
| 6 to 15 | 0.0 | 0.0 | 6.7 | 3.3 | 13.3 | 3.3 | 3.3 | 0.0 | 13.3 | 3.3 | 0.0 | 0.0 |
| 0-5 | 10.0 | 0.0 | 6.7 | 3.3 | 6.7 | 0.0 | 6.7 | 3.3 | 3.3 | 3.3 | 3.4 | 3.3 |

No B-glucan                              + B-glucan

Fig. 4

SERUM FREE INTRACELLULAR PATHOGEN VACCINE

CROSS-REFERENCE TO RELATED APPLICATIONS

This application is a National Stage application of International Patent Application No. PCT/EP2019/086630, filed Dec. 20, 2019, which claims priority to EP18215363.5, filed Dec. 21, 2018.

FIELD OF THE INVENTION

The present invention is related to a vaccine, more particularly to fish vaccines. The present invention is related to vaccine comprising an intracellular pathogen antigen. The present invention is related to vaccine compositions that have little or are substantially free of albumin or serum. The present invention is also related to the prevention or reduction of cross-stitch spinal deformities in an animal by the use of vaccines comprising an intracellular pathogen antigen and little or no albumin or serum.

BACKGROUND

Vertebral column malformations in fish occur under farming conditions and in wild specimens and were recognised as a problem as early as 1981. The vertebral deformities are recognised as individuals with anomalous body shape, often shorter and more compressed than normal and with a humpback appearance. Often the occurrence is not fully recognised until harvest size, as the severity of the lesions seems to develop during seawater rearing. The problem causes economic loss to fish farmers and may also compromise animal welfare. Fish with spinal deformities, such as salmon, trout, cod, halibut, sea bass and sea bream, do not swim efficiently, are less capable of acquiring food, are at a greater risk of predation and are more susceptible to physiological imbalance, in addition to being down-graded at slaughter. Also fish with deformities may cause technical problems to filleting equipment.

Bone deformities can appear in both early and late life stages and it has been suggested that the condition has a multifactorial aetiology. It has been shown that environmental factors, such as high temperature during egg incubation and in the freshwater phase, may induce spinal deformities. Nutritional and microbial factors have further been associated with skeletal malformation in various fish species. An indication that vaccines constitute a risk factor for the development of spinal deformities was reported in an epidemiological study for the first time in 1998, but the low number of groups available for comparison limited any firm conclusions.

Different types of vertebral column malformations exist and can be distinguished from each other by X-ray. The most prominent feature on radiographs of salmon vertebral bodies is a radio dense symmetrical X-shaped structure. Vertebral columns without signs of deformations show a homogenous shape and size of the vertebral bodies throughout the spine (see FIG. 1A). Witten et al. (Aquaculture 295 (2009), p 6-14) distinguishes 20 different types of deformities. In some cases, the intervertebral space is decreased with or without vertebral fusion, or the intervertebral space is increased. In other cases, the vertebrae are compressed and may be altered in shape. Also, the vertebrae may be fused to some extent or completely fused. Furthermore, one or more vertebrae may be shifted vertically. In a particular spinal deformity, the intervertebral space is completely collapsed, and this is also known as "cross-stitch vertebrae", see for example FIG. 1B.

An object of the present invention is to reduce the spinal deformities in an animal, preferably fish. Another object of the invention is to reduce the incidence and/or severity of cross-stitch vertebrae particularly in fish.

It was surprisingly found that one or more objects can be met by a vaccine composition comprising a low amount, or even essentially, no albumin protein. Furthermore, it was surprisingly found that one or more objects can be met by a vaccine composition comprising a low amount, or even essentially, no serum.

SUMMARY OF THE INVENTION

The invention relates to a vaccine composition comprising an antigen from an intracellular pathogen, wherein the composition comprises less than 5% v/v of serum, The invention relates to a vaccine composition comprising an antigen from an intracellular pathogen, wherein the composition comprises less than 5% v/v of serum, and wherein the pathogen is a virus, an intracellular bacterium or an intracellular parasite.

The invention also relates to a vaccine composition comprising an antigen from an intracellular pathogen, wherein the composition comprises less than 2.5 g/L of albumin.

The invention also relates to a vaccine composition comprising an antigen from an intracellular pathogen, wherein the composition comprises less than 0.5 g/L of post-translational modified albumin.

The invention also relates to a vaccine composition comprising an antigen from an intracellular pathogen, wherein the composition comprises less than 2.5 g/L native albumin.

In a preferred embodiment of the present invention and/or embodiments thereof, the intracellular pathogen is a virus. In a preferred embodiment of the present invention and/or embodiments thereof, the pathogen is a fish virus, preferably the pathogen is a salmon virus. Suitably virus according to the invention and/or embodiments thereof may be selected from the group comprising salmon alpha virus (SAV), Red Sea bream iridovirus (RSIV), Infectious Haematopoietic Necrosis virus (IHNV), viral Haemorrhagic Septicaemia virus (VHSV), Infectious Salmon Anaemia virus (ISAV), channel Catfish virus (CCV), Spring Viraemia of Carp virus (SVCV), Nervous Necrosis virus (NNV), Grass Carp haemorrhage disease virus (GCHDV), Tilapia Lake virus (TLV), marine aquabimavirus (MABV), Epizootic Hematopoietic Necrosis virus (EHNV), Piscine Reovirus (PRV), and Cardiomyopathy Virus (CMV). In a preferred embodiment of the present invention and/or embodiments thereof the vaccine composition does not comprise Infectious Pancreatic Necrosis virus (IPNV).). In a preferred embodiment of the present invention and/or embodiments thereof the pathogen is salmon alpha virus (SAV).

The invention relates to a vaccine composition comprising an antigen from an intracellular bacterium wherein the composition comprises less than 5% v/v of serum.

The invention also relates to a vaccine composition comprising an antigen from an intracellular bacterium wherein, the composition comprises less than 2.5 g/L of albumin.

The invention also relates to a vaccine composition comprising an antigen from an intracellular bacterium, wherein the composition comprises less than 0.5 g/L of post-translational modified albumin.

The invention also relates to a vaccine composition comprising an antigen from an intracellular bacterium wherein the composition comprises less than 2.5 g/L native albumin.

A suitable intracellular bacterium is selected from the group comprising *Piscirickettsia, Franciscella*, Chlamidia, *Rickettsia, Coxiella*, In a preferred embodiment of the present invention and/or embodiments thereof, the intracellular bacterium is a fish intracellular bacterium. Suitable intracellular bacterium is selected from the group comprising *Piscirickettsia*, and *Franciscella*. Suitably the intracellular bacterium is *Piscirickettsia salmonis*, or *Francisella philomiragia*, or *Francisella tularensis*.

The invention relates to a vaccine composition comprising an antigen from an intracellular parasite, wherein the composition comprises less than 5% v/v of serum.

The invention also relates to a vaccine composition comprising an antigen from an intracellular parasite wherein the composition comprises less than 2.5 g/L of albumin.

The invention also relates to a vaccine composition comprising an antigen from an intracellular parasite, wherein the composition comprises less than 0.5 g/L of post-translational modified albumin.

The invention also relates to a vaccine composition comprising an antigen from an intracellular parasite, wherein the composition comprises less than 2.5 g/L native albumin.

Suitable intracellular parasite is selected from the group comprising Apicomplexa, Microsporidia and *Trypanosoma*. In a preferred embodiment of the invention and/or embodiments thereof the intracellular parasite is Apicomplexa or Microsporidia. Suitable apicomplexa are Coccidia, Cryptosporidia Octosporella, and *Isospora*.

In a preferred embodiment of the present invention and/or embodiments thereof, the vaccine comprises less than 2 g/L, more preferably less than 1 g/L, more preferably less than 0.8 g/L, even more preferably less than 0.5 g/L more preferably less than 0.1 g/L even more preferably less than 0.05 g/L, more preferably less than 0.01 g/L of albumin.

In a preferred embodiment of the present invention and/or embodiments thereof, the vaccine comprises less than 0.5 g/L, more preferably less than 0.1 g/L, more preferably less than 10 mg/L, even more preferably less than 1 mg/L more preferably less than 0.1 mg/L even more preferably less than 50 μg/L, more preferably less than 10 μg/L of post-translational modified albumin.

In a preferred embodiment of the present invention and/or embodiments thereof, the vaccine comprises less than 2 g/L, more preferably less than 1 g/L, more preferably less than 0.8 g/L, even more preferably less than 0.5 g/L more preferably less than 0.1 g/L even more preferably less than 0.05 g/L, more preferably less than 0.01 g/L of native albumin.

In a preferred embodiment of the present invention and/or embodiments thereof, the vaccine comprises less than 4% (v/v) of serum, more preferably less than 3% (v/v) of serum, more preferably less than 2.5% (v/v) of serum, even more preferably less than 2% (v/v) of serum, even more preferably less than 1.5% (v/v) of serum, even more preferably less than 1.2% (v/v) of serum, more preferably less than 1% (v/v) of serum, more preferably less than 0.8% (v/v) of serum, even more preferably less than 0.5% (v/v) of serum, even more preferably less than 0.4% (v/v) of serum, even more preferably less than 0.3% (v/v) of serum, more preferably less than 0.2% (v/v) of serum, even more preferably less than 0.1% (v/v) of serum, even more preferably less than 0.05% (v/v) of serum.

In a preferred embodiment of the present invention and/or embodiments thereof the serum is sourced from the group consisting of bovine, sheep, chicken, goat, horse, lamb, newborn calf, porcine, rabbit. The serum may be modified.

In a preferred embodiment of the present invention and/or embodiments thereof the serum is fetal calf serum, fetal bovine serum, or new born calf serum.

The invention is further directed to a vaccine composition comprising an antigen from an intracellular pathogen for use to prevent, treat, or reduce a disease caused by the intracellular pathogen and to prevent, avoid, or reduce the incidence of cross-stitch spinal deformity in an animal, wherein the composition comprises less than 5% v/v of serum.

The invention is further directed to a vaccine composition comprising an antigen of an intracellular pathogen for use to prevent, treat, or reduce a disease caused by the intracellular pathogen and to prevent, avoid, or reduce the incidence of cross-stitch spinal deformity in an animal, wherein the composition comprises less than less than 2.5 g/L of albumin.

The invention is further directed to a vaccine composition comprising an intracellular pathogen antigen for use to prevent, treat, or reduce a disease caused by the intracellular pathogen and to prevent, avoid, or reduce the incidence cross-stitch spinal deformity in an animal, wherein the composition comprises less than less than 0.5 g/L of post-translational modified albumin.

The invention is further directed to a vaccine composition comprising an intracellular pathogen antigen for use to prevent, treat, or reduce a disease caused by the intracellular pathogen and to prevent, avoid, or reduce the incidence cross-stitch spinal deformity in an animal, wherein the composition comprises less than less than 2.5 g/L of native albumin.

The animal is preferably a fish. The intracellular pathogen is preferably a fish pathogen. The intracellular pathogen is preferably salmon alpha virus (SAV).

DETAILED DESCRIPTION OF THE INVENTION

Legend to the Figures

FIG. 1: X-ray of normal vertebrae (A) and of vertebrae with cross-stitch pathology (B)

FIG. 2: fish with cross-stitch pathology as determined by X-ray. Categories are indicated by the number of affected vertebrae. Results from fish on a diet without β-glucan (A-C1-A-C6) and from fish on a diet with β-glucan (B-C1-B-C6).

Figure 3:
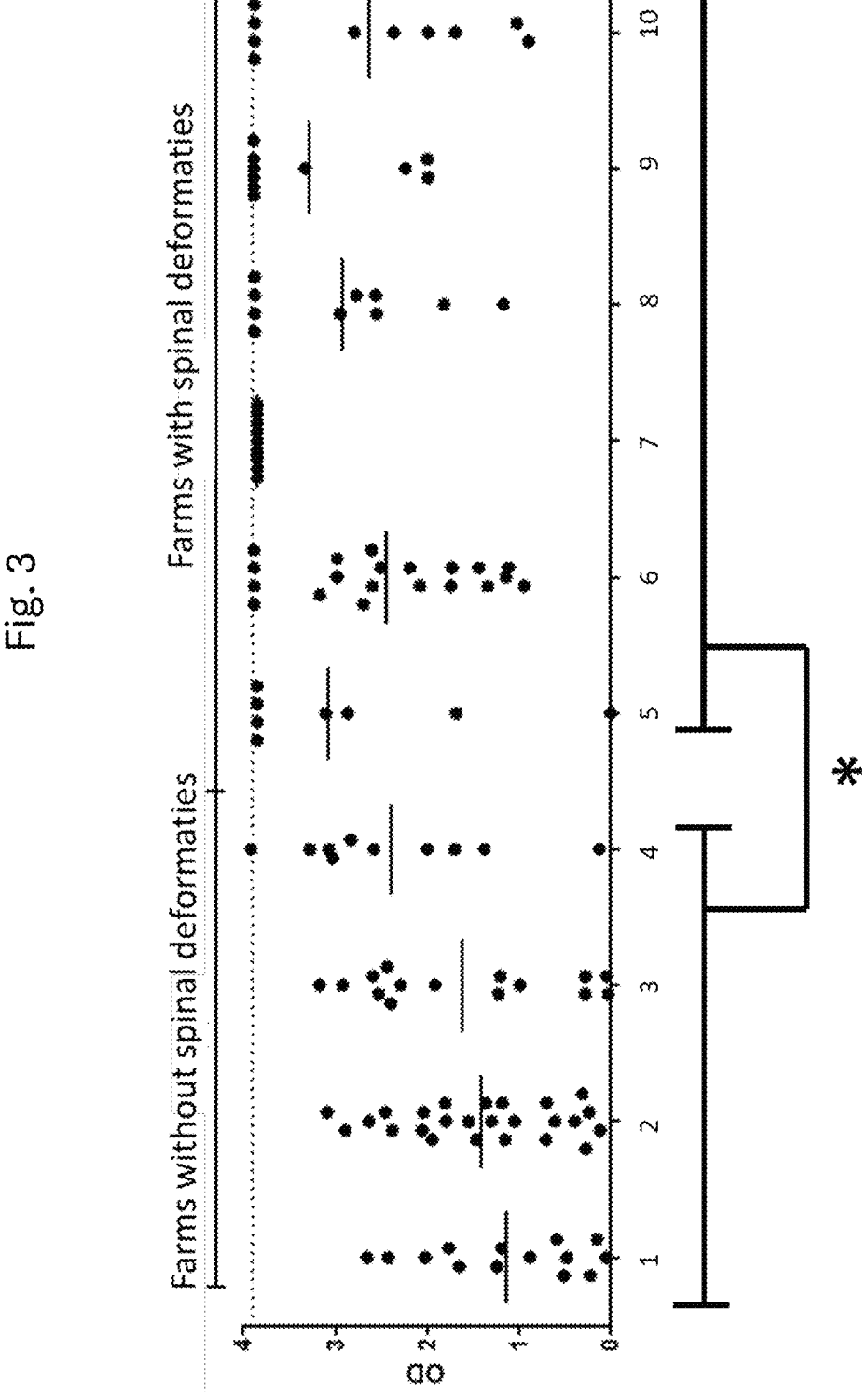

FIG. 3 Elisa results from farms where no spinal deformities were observed (1-4) and from farms where spinal deformities were observed (5-10). The * indicates that there is a significant difference between the Elisa results.

Figure 4:
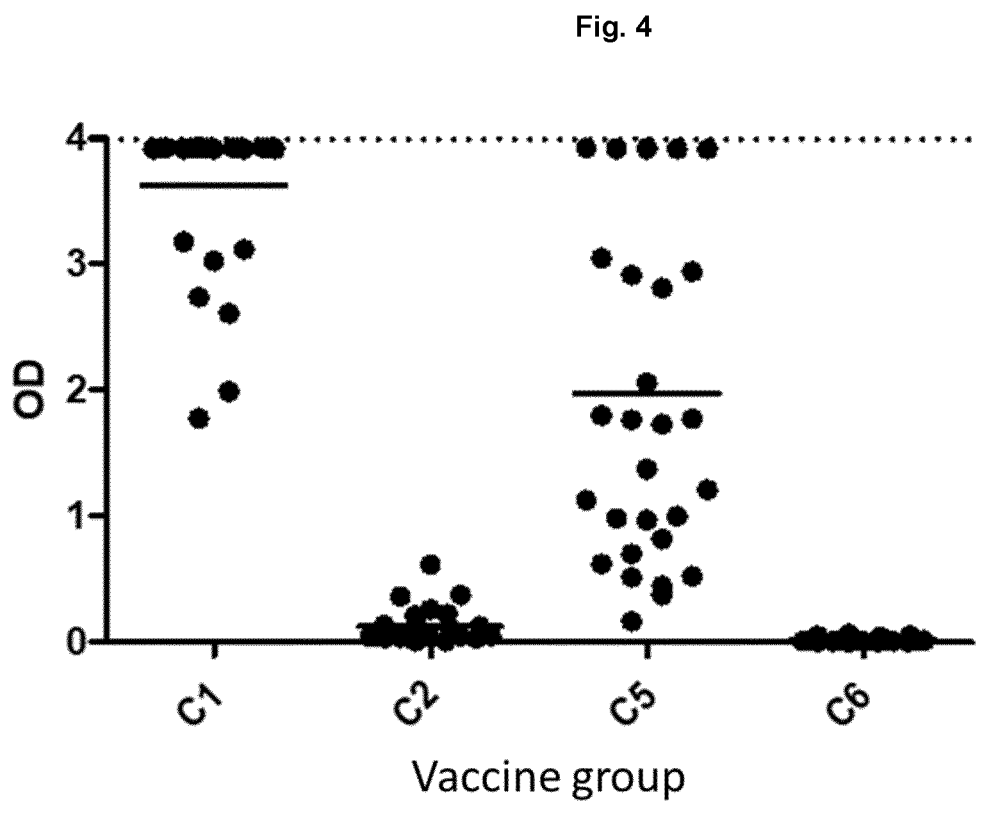

FIG. 4 Elisa results from the vaccination groups of experiment 1, C1, C2, C5 and C6.

Figure 5:
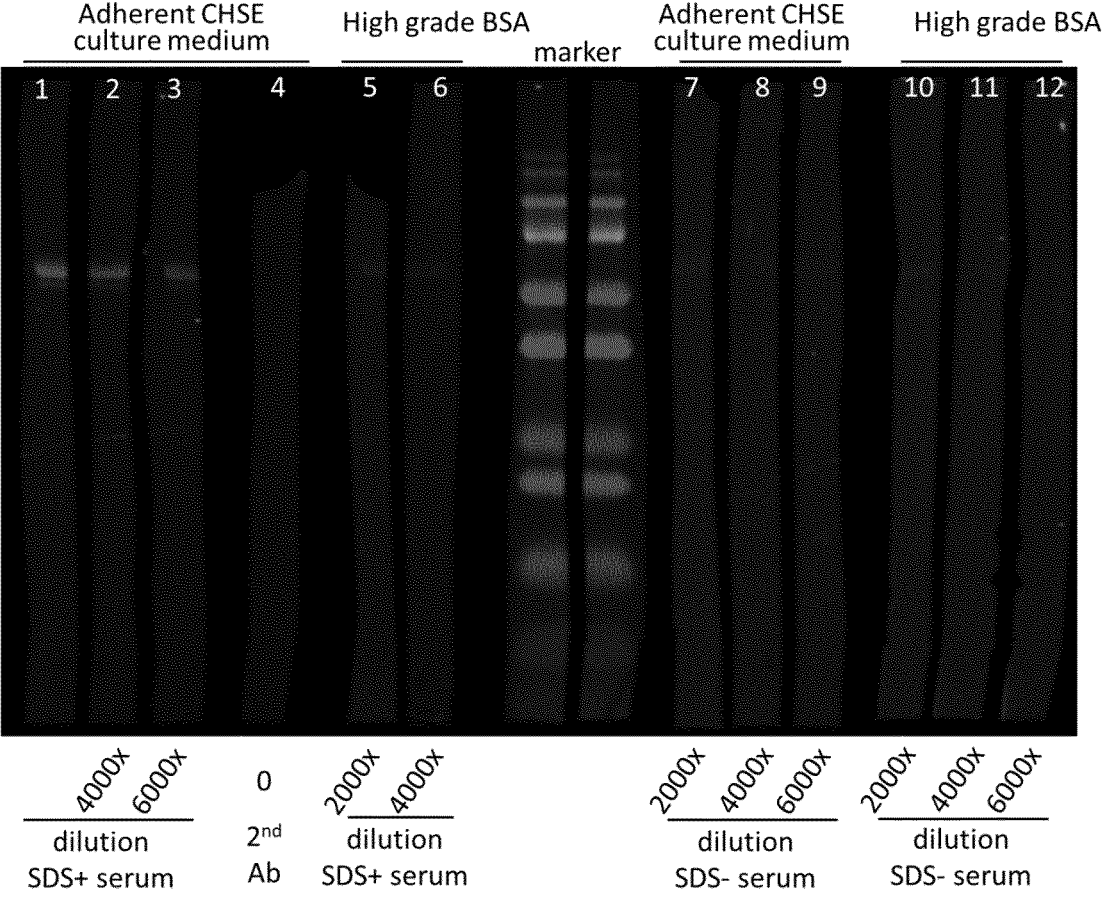

FIG. 5: Western blot of serum from fish positive for spinal deformities and fish negative for spinal deformities.

The invention relates to a vaccine composition comprising little or even no serum. Intracellular pathogens such as viruses, intracellular bacteria and intracellular parasites for vaccine are grown in cells that grow in medium that is often supplemented with serum.

Animal sera—both bovine and non-bovine sera—are used in cell culture applications with the most widely used being fetal bovine serum (FBS). Serum contains growth factors and very low levels of antibodies, allowing for versatility in many different cell culture applications. There are 1000+ components found in serum such as FBS, including proteins, electrolytes, lipids, carbohydrates, hormones, enzymes, and other undefined constituents, which are necessary in many culture conditions to support cell growth. Serum is typically used in concentrations of 5-10% in a medium. Serum is a natural product, and its composition is undefined and varies from lot-to-lot.

Serum is the liquid fraction of clotted blood. It is depleted of cells, fibrin and clotting factors. Serum differs from plasma in that anti-coagulant is never added to the blood after collection from the animal. Serum may be prepared by centrifuging until the clot and remaining blood cells are separated from the liquid phase. The serum may then be removed and stored frozen pending further processing. The first stage of the production process for fetal bovine serum is the harvesting of blood from the bovine fetus after the fetus is removed from the slaughtered cow. The blood is collected aseptically into a sterile container or blood bag and then allowed to clot. The normal method of collection is cardiac puncture, wherein a needle is inserted into the heart. This minimizes "the danger of serum contamination with micro-organisms from the fetus itself, and the environment. It is then centrifuged to remove the fibrin clot and the remaining blood cells from the clear yellow (straw) colored serum. The serum is frozen prior to further processing that is necessary to make it suitable for cell culture.

The second stage of processing involves filtration, typically using a filtration chain with the final filtration being triple sterile 0.1 micrometre membrane filters. When processed by a reputable commercial serum supplier, the sterilized fetal bovine serum is subjected to stringent quality control testing. FBS contains a complex array of protein components that are required by many cells to grow which is why it has been successfully used in cell culture.

The serum may be sourced from animals such as bovine, sheep, chicken, goat, horse, lamb, newborn calf, avian, porcine, piscine, or rabbit. Preferred serum is bovine serum, and most preferred is fetal calf serum, fetal bovine serum, or new born calf serum. The serum may be modified.

Fetal Bovine Serum

Fetal bovine serum (FBS) also known as Fetal Calf Serum (FCS) is obtained as described above from the blood of fetuses of healthy, pre-partum bovine dams that have been ante- and/or post-mortem veterinary inspection. Fetal blood is collected aseptically using cardiac puncture, thereby reducing the risk of microbial contamination and resultant endotoxins. Sometimes FBS sterile filtered and may be subjected to one or more modification processes. Examples are Dialyzed, Charcoal Stripped, Ultra-low IgG, ES Cell, MSC and Exosome-Depleted.

Newborn Calf Serum

Newborn Calf Serum (NBCS) is defined as the liquid fraction of clotted blood derived from healthy, slaughtered bovine calves aged less than 20 days, deemed fit for human consumption through ante- and/or post-mortem inspection.

Donor Bovine Serum (Also Known Donor Calf Serum)

Donor-sourced Bovine Serum (DBS) is defined as the liquid fraction of clotted blood derived from healthy cattle 12 months of age or older from controlled donor herds whose health status is confirmed by regular inspection by competent, legally authorized veterinarians.

Bovine Serum (Also Known as Adult Bovine or Calf Serum)

Bovine Serum is defined as the liquid fraction of clotted blood derived from healthy, slaughtered cattle 12 months of age or older, deemed to be fit for human consumption by ante- and/or post-mortem inspection.

The globular protein, bovine serum albumin (BSA), is a major component of fetal bovine serum. The rich variety of proteins in fetal bovine serum maintains cultured cells in a medium in which they can survive, grow, and divide.

The inventors found that fish that were vaccinated with vaccines that comprise bovine serum, which comes from the growth medium of the intracellular pathogen component, have a much higher risk of developing cross-stitch spinal deformities than fish vaccinated with vaccines without serum. In addition, it was found that sera, from vaccinated fish from farms where spinal deformities were found, reacted with the culture medium of the cells where the intracellular pathogen component of the vaccine was grown in. In contrast sera from vaccinated fish from farms where no spinal deformities were seen did not or very little react with culture medium.

Therefore, the vaccines of the present invention and/or embodiments thereof, comprises as little as possible serum and preferably no serum at all. Preferably the vaccine comprises less than 5% of serum, preferably less than 4% of serum, more preferably less than 3% of serum, more preferably less than 2.5% of serum, even more preferably less than 2% of serum, even more preferably less than 1.5% of serum, even more preferably less than 1.2% of serum, more preferably less than 1% of serum, more preferably less than 0.8% of serum, even more preferably less than 0.5% of serum, even more preferably less than 0.4% of serum, even more preferably less than 0.3% of serum, more preferably less than 0.2% of serum, even more preferably less than 0.1% of serum, even more preferably less than 0.05% of serum. Even more preferably, the vaccine comprises less than 0.01% serum, or even less than 0.005% or even less, and most preferably substantially no serum. Serum may be removed from the intracellular pathogen harvested from the culture, by filtration, ultracentrifugation. Preferably the intracellular pathogen comes from a culture that is serum-free. Methods to grow cells that are infected by intracellular pathogens in a serum-free medium are known to the art, such as U.S. Pat. Nos. 9,441,207, 5,753,489, WO2001064846, U.S. Pat. No. 665,671.

The invention also relates to a vaccine composition comprising little or even no albumin. Albumin comes from serum and the most common albumin is bovine serum albumin (also known as BSA or "Fraction V"). It is a serum albumin protein derived from cows. It is often used as a protein concentration standard in lab experiments. The nickname "Fraction V" refers to albumin being the fifth fraction of the original Edwin Cohn purification methodology that made use of differential solubility characteristics of plasma proteins. By manipulating solvent concentrations, pH, salt levels, and temperature, Cohn was able to pull out successive "fractions" of blood plasma. The process was first commercialized with human albumin for medical use and later adopted for production of BSA. Albumin may however also be sourced from bovine, sheep, chicken, goat, horse, lamb, newborn calf, porcine, or rabbit. Serum albumin is the most abundant proteins in blood plasma. The concentration of serum albumin in serum is about 35 to 50 g/L.

In a preferred embodiment of the present invention and/or embodiments thereof, the vaccine comprises less than 2 g/L, more preferably less than 1 g/L, more preferably less than 0.8 g/L, even more preferably less than 0.5 g/L more preferably less than 0.1 g/L even more preferably less than 0.05 g/L, more preferably less than 0.01 g/L of albumin.

Native albumin is the largest fraction of albumin in serum. Native albumin is not modified. In a preferred embodiment of the present invention and/or embodiments thereof, the vaccine comprises less than 2 g/L, more preferably less than 1 g/L, more preferably less than 0.8 g/L, even more preferably less than 0.5 g/L more preferably less than 0.1 g/L even more preferably less than 0.05 g/L, more preferably less than 0.01 g/L of native albumin.

The invention also relates to a vaccine composition comprising little or even no post-translational modified albumin. In the mammal, serum albumin undergoes post-translational modifications. Posttranslational modifications of proteins are important reactions which significantly affect the function of proteins in the body. In principle, they can be divided into enzymatic and non-enzymatic modifications. Non-enzymatic reactions include glycation, which plays an important role in the chronic complications of diabetes mellitus, uremia, in the process of aging and degeneration of the brain.

In the non-enzymatic glycation of proteins (earlier called non-enzymatic glycosylation), free amino groups of peptides/proteins react with the carbonyl groups of reducing sugars without the catalytic action of enzymes. This reaction was first described by Louis Maillard, who observed a browning of proteins in their heating with sugars. Initially it appeared that this reaction is only relevant in food chemistry, but in 1971 it was found that glycation takes place in every living organism, especially if the concentration of sugar in the blood is increased. Other modifications include cysteinylation, S-nitrosylation, S-transnitrosation and S-guanylation, most often on cysteine residues.

Another post-translation modification is carbamylation. Carbamylation is a non-enzymatic and irreversible post-translational modification (PTM) that mainly results from interaction between isocyanic acid and amino groups of proteins. When this occurs on lysine residues within polypeptide chains, ε-carbamyl-lysine (i.e., homocitrulline) is generated. Isocyanic acid is mainly produced from the spontaneous decomposition of urea into ammonium and cyanate, a reactive species that is rapidly converted to isocyanic acid. Reactive cyanate may also be generated from thiocyanate metabolism. Neutrophil-derived myeloperoxidase (MPO) catalyzes the oxidation of thiocyanate in the presence of hydrogen peroxide. This occurs at sites of inflammation and atherosclerotic plaque, where thiocyanate is abundant in blood.

Citrullination and carbamylation are two post-translational modifications that result in the generation of citrulline and homocitrulline, two highly related, non-standard amino acids. Citrullination of arginine is catalyzed by peptidylarginine deiminases (PADs).

Post-translational modifications of proteins occurs in healthy individuals and may be increased in several clinical conditions such as atherosclerosis, kidney disease, and inflammation.

In a preferred embodiment of the present invention and/or embodiments thereof, the vaccine comprises less than 2 g/L, more preferably less than 1 g/L, more preferably less than 0.8 g/L, even more preferably less than 0.5 g/L, more preferably less than 0.2 g/L, more preferably less than 0.1 g/L, even more preferably less than 0.05 g/L, more preferably less than 0.02 g/L, more preferably less than 0.01 g/L of post-translational modified albumin. In a preferred embodiment of the present invention and/or embodiments thereof, the vaccine comprises less than 2 mg/L, more preferably less than 1 mg/L, more preferably less than 0.8 mg/L, even more preferably less than 0.5 mg/L, more preferably less than 0.2 mg/L, more preferably less than 0.1 mg/L, even more preferably less than 0.05 mg/L, more preferably less than 0.02 mg/L, more preferably less than 0.01 mg/L of post-translational modified albumin. In a preferred embodiment of the present invention and/or embodiments thereof, the vaccine comprises less than 2

µg/L, more preferably less than 1 µg/L, more preferably less than 0.8 µg/L, even more preferably less than 0.5 µg/L, more preferably less than 0.2 µg/L, more preferably less than 0.1 µg/L, even more preferably less than 0.05 µg/L, more preferably less than 0.02 µg/L, more preferably less than 0.01 µg/L of post-translational modified albumin.

In a preferred embodiment of the present invention and/or embodiments thereof, the post-translational modification of the albumin is selected from the group consisting of citrullination, carbamylation, glycation, cysteinylation, S-nitrosylation, S-transnitrosation and S-guanylation. In a preferred embodiment of the present invention and/or embodiments thereof, the post-translational modification of the albumin is selected from the group consisting of citrullination, carbamylation, glycation, cysteinylation. In a preferred embodiment of the present invention and/or embodiments thereof, the post-translational modification of the albumin is selected from the group consisting of citrullination, carbamylation, glycation. In a preferred embodiment of the present invention and/or embodiments thereof, the post-translational modification of the albumin is citrullination. In a preferred embodiment of the present invention and/or embodiments thereof, the post-translational modification of the albumin is carbamylation. In a preferred embodiment of the present invention and/or embodiments thereof, the post-translational modification of the albumin is glycation.

Albumin may be removed from the intracellular pathogen harvested from the culture, by washing, or affinity resins with antibodies against albumin or specific albumins, salt precipitation such as with ammonium sulphate and sodium sulphate, size exclusion chromatography or centrifugation. Also specific albumin removal kits exists such ProteoExtract kits. Preferably the intracellular pathogen comes from a culture that is albumin-free. Methods to grow cells that are infected by intracellular pathogens in an albumin-free or low-albumin medium are known from U.S. Pat. No. 665, 671.

The antigen of the vaccine of the present invention comes from an intracellular pathogen that has been grown on a cell-culture. The antigen may be a whole pathogen or derived from a whole pathogen. The pathogen may be a live, killed or attenuated pathogen. Derived from a whole pathogen means that at some point in the derivation there was a whole pathogen, e.g. from an inactivation method. A whole pathogen or derived from a whole pathogen, does not include plasmids, DNA, expression particles, replicon particles and the like. Subunit and recombinant vaccines may be encompassed by the present invention especially when the antigen is a subunit or recombinant protein that is produced in a cell culture or is derived from a pathogen that is cultured in a cell culture.

In a preferred embodiment of the present invention and/or embodiments thereof, the antigen is a virus. In a preferred embodiment of the present invention and/or embodiments thereof, the antigen is a fish virus antigen, preferably a salmon virus antigen.

A "fish" refers to fin fish, both cartilaginous and bony fin fish, of any climate area: cold-, temperate- or tropical waters, and living in sweet-, brackish, or salt water. The fish may be grown in captivity as farmed fish, breeding fish or ornamental fish. Preferably a fish is selected from: bass, grouper, snapper, Tilapia, yellowtail, amberjack, flounder, Pangasius, carp, bream, sturgeon, catfish, eel, trout, salmon, whitefish, halibut, cod, Koi, and goldfish.

In an embodiment the fish is a salmonid fish; preferably the salmonid fish is selected from Atlantic-, steelhead-, chinook-, coho-, pink-, chum-, and sockeye salmon, rainbow-, brook-, lake-, and brown trout, and char.

Fish cells like salmon CHSE cells and carp FHMP cells can be grown in a serum free medium by repeating and selecting cells that grow well in a medium with increasingly less serum, until there is no serum present in the medium.

Shea and Berry (In Vitro vol 19, no. 11, (1983), p 818-825) discloses that a range of fish cell lines can be grown on serum free medium, including CHSE-214 cells and were able to support the replication of gold-fish virus-2 at levels equivalent to cells grown in medium with serum.

PD virus can be cultured on CHSE-214 cells in serum free medium. JP2003219873 discloses CHSE-214 cells that grow in suspension and can be cultured serum-free medium. Also other fish cells have been reported capable of growing in suspension. One is a method of culturing CHSE-214 cells (a cell line derived from a king salmon embryo) in a suspended EMEM-S culture solution containing carboxymethyl cellulose (Lidgerding, Develop. Biol. Standard, 49, 233-241 (1981)), and the other is a method using the MB752/1 medium of Waymouse without CaCl2 (Hasobe M., et al., Bull. Eur. Asso. Fish Pathol., 11, 142-144 (1991)).

JP2003219873 discloses that the suspensions CHSE-214 cells can be cultured in serum free medium and that they can be saved at low temperature such as about 4 degrees Celsius. JP2003219873 discloses that the CHSE-214 suspension cells can be cultured in serum free culture with addition of lactalbumine hydrolysate as serum substitute. A suitable medium is Waymouth medium MB752/1 without addition of CaCl2, 14 mM Hepes (pH adjustment with NaOH), 10% lactalbumin hydrolysate aqueous solution 5% and kanamycin 0.06 g/L added. The medium has a pH of 7.4.

Serum free medium is commercially available. As substituent for serum or albumin, yeast extracts or wheat gluten hydrolasates may be used. WO099/57246 discloses serum free cell culture medium completely devoid of animal proteins and lipids. In here the protein is derived from rice, soy, potato, corn and aloe vera and the lipid is derived from rice, soy, potato, corn and aloe vera as well as from bacteria, yeast and fungi.

KR20160074818 discloses culturing a fish virus, Megalocytivirus, using Serum Free Medium in a Sea Bream cell line (Pagrus majorfin (PMF) cells.

Suitably virus antigen according to the invention and/or embodiments thereof may be selected from the group comprising salmon alpha virus (SAV), Red Sea bream iridovirus (RSIV), Infectious Haematopoietic Necrosis virus (IHNV), viral Haemorrhagic Septicaemia virus (VHSV), Infectious Salmon Anaemia virus (ISAV), channel Catfish virus (CCV), Spring Viraemia of Carp virus (SVCV), Nervous Necrosis virus (NNV), Grass Carp haemorrhage disease virus (GCHDV), Tilapia Lake virus (TLV), marine aquabimavirus (MABV), Epizootic Hematopoietic Necrosis virus (EHNV), Piscine Reovirus (PRV), and Cardiomyopathy Virus (CMV).

In a preferred embodiment of the present invention and/or embodiments thereof the vaccine composition does not comprise Infectious Pancreatic Necrosis virus (IPNV). In a preferred embodiment of the present invention and/or embodiments thereof, the virus antigen is selected from the group comprising salmon alpha virus (SAV), Infectious Haematopoietic Necrosis virus (IHNV), Infectious Salmon Anaemia virus (ISAV), Tilapia Lake virus (TLV), Piscine Reovirus (PRV), and Cardiomyopathy Virus (CMV) and Epizootic Hematopoietic Necrosis virus (EHNV). In a preferred embodiment of the present invention and/or embodiments thereof, the virus antigen is selected from the group comprising salmon alpha virus (SAV), Infectious Infectious Salmon Anaemia virus (ISAV), Piscine Reovirus (PRV), Cardiomyopathy Virus (CMV), and Tilapia Lake virus (TLV). In a preferred embodiment of the present invention and/or embodiments thereof, the virus antigen is salmon alpha virus (SAV), Piscine Reovirus (PRV), and Cardiomyopathy Virus (CMV). In a preferred embodiment of the present invention and/or embodiments thereof, the virus antigen is salmon alpha virus (SAV).

In a preferred embodiment of the present invention and/or embodiments thereof, the antigen is intracellular bacterium. In a preferred embodiment of the present invention and/or embodiments thereof, the intracellular bacterium is selected from the group comprising Piscirickettsia, Franciscella, Chlamidia, Rickettsia, Coxiella, In a preferred embodiment of the present invention and/or embodiments thereof, the intracellular bacterium is a fish intracellular bacterium. Suitable intracellular bacterium is selected from the group comprising Piscirickettsia, and Franciscella. Suitably the intracellular bacterium is Piscirickettsia salmonis, or Francisella philomiragia, or Francisella tularensis.

In a preferred embodiment of the present invention and/or embodiments thereof, the antigen is an intracellular parasite. In a preferred embodiment of the present invention and/or embodiments thereof, the intracellular parasite is selected from the group comprising Apicomplexa, Microsporidia and Trypanosoma. In a preferred embodiment of the invention and/or embodiments thereof the intracellular parasite is Apicomplexa or Microsporidia. Suitable apicomplexa are Coccidia, Cryptosporidia Octosporella, and Isospora.

Vaccines are often emulsions. An "emulsion" is a mixture of at least two immiscible liquids, whereby one is dispersed in another. Typically the droplets of the dispersed phase are very small, with diameters of a few micrometers or less. Procedures and equipment for the preparation of an emulsion at any scale are well-known in the art, and are for instance described in handbooks such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN 0444819681).

The vaccines of the present invention may contain additional antigens, such bacterial antigens, DNA, plasmids, replican particle and the like. A bacterial antigen may be a live bacterium, a killed bacterium or an attenuated bacterium, or a bacterin.

A "vaccine" is a well-known composition with a medical effect, and comprises an immunologically active component, and a pharmaceutically acceptable carrier. The 'carrier' may be the aqueous phase, or the emulsion itself. The 'immunologically active component' for the invention is the antigen from the intracellular pathogen. The vaccine stimulates the immune system of a target animal, and induces a protective immunological response. The response may originate from the targets' innate- and/or from the acquired immune system, and may be of the cellular- and/or of the humoral type.

A vaccine provides "protection" "against infection or disease" by reducing in a vaccinated target the severity of a subsequent infection, by for example reducing the number of pathogens, or shortening the duration of the pathogen's replication in the target, and reducing the number, the intensity, or the severity of lesions caused by a bacterial infection. Also, or consequentially, a vaccine is effective in reducing or ameliorating the (clinical) symptoms of disease that may be caused by such infection or replication, or by the target's response to that infection or replication. A reference for such diseases and clinical signs is: "The Merck veterinary manual" (10th ed., 2010, C. M. Kahn edt., ISBN: 091191093X. Such a vaccine is colloquially referred to as a: vaccine 'against' the particular bacterium, or as a 'bacterial vaccine'.

In order to be immunologically effective, a vaccine needs to contain a sufficient amount of the antigen. How much that is, is either already known from related vaccines, or can readily be determined e.g. by monitoring the immunological response following vaccination and (in the case of an animal target) a challenge infection, e.g. by monitoring the targets' signs of disease, clinical scores, or by re-isolation of the pathogen, and comparing these results to a vaccination-challenge response seen in mock-vaccinated animals.

The vaccine according to the invention can be used as a prophylactic-, metaphylactic-, or therapeutic treatment.

The vaccine according to the invention can serve as an effective priming vaccination, which can later be followed and amplified by a booster vaccination, with the same or with a different vaccine.

The vaccine according to the invention prevents, reduces or avoids spinal deformities and especially cross-stitch spinal deformities in the animal vaccinated. The reduction, prevention or avoidance of spinal deformities is when compared to animals having been treated with a vaccine containing the same antigens however with more than 5% serum or more than 2.5 g/L of albumin.

The vaccine according to the invention can additionally comprise other compounds, such as an additional antigen or micro-organism, a cytokine, or an immunostimulatory nucleic acid comprising an unmethylated CpG, etc.

The vaccine according to the invention can advantageously be combined with one or more further antigens, e.g. derived from a micro-organism pathogenic to the animal target. Such a further antigen may itself be an infectious micro-organism, or be inactivated, or a subunit. The further antigen may consist of a biologic or synthetic molecule such as a protein, a carbohydrate, a lipopolysacharide, a lipid, or a nucleic acid molecule.

For vaccination of ruminants the additional antigen from a pathogen is selected from one of: *Pasteurella, Escherichia, Salmonella, Yersinia, Staphylococcus, Streptococcus, mycoplasma, Moraxella, Bacillus, Brucella,* Clostridia, *Mannheimia, Haemophilus, Francisella,* Fusobacteria, *Histophilus, Trueperella* (Arcanobacteria), *Actinomyces, Clostridium, Coxiella, Campylobacter, Erysipelothrix, Leptospira, Listeria, Burkholderia, Nocardia, Mycoplasma, Bacteroides,* and *Chlamydia.*

For vaccination of porcines the additional antigen from a pathogen is selected from one of *Mycoplasma, Lawsonia, Escherichia, Brachyspira, Streptococcus, Salmonella, Clostridium, Actinobacillus, Pasteurella, Haemophilus, Erysipelothrix, Leptospira, Burkholderia, Enterococcus, Mycoplasma,* and *Bordetella.*

For vaccination of poultry the additional antigen from a pathogen is selected from one of: *Escherichia, Salmonella, Staphylococcus, Streptococcus,* Omitoadditional pathogen, Aviadditional pathogen, *Haemophilus, Pasteurella, Erysipelothrix, Mycoplasma,* Mycoadditional pathogen, *Clostridium, Campylobacter, Shigella, Borrelia, Enterococcus, Listeria, Riemerella, Bordetella,* and *Clostridium.*

For vaccination of an animal of aquatic nature, the additional antigen from a pathogen is selected from one of: *Aeromonas, Vibrio, Moritella, Edwardsiella, Francisella, Flexibacter, Pasteurella, Cytophaga,* Coryneabacteria, Renibacteria, *Arthrobacter, Flavobacteria, Fusarium, Bacillus, Yersinia, Mycobacteria, Neorickettsia, Listonella, Flexi-*

*bacter, Piscirickettsia, Streptococcus, Shewanella, Pseudomonas, Photobacteria, Clostridium, Tenacibaculum, Lactococcus, Leucothrix,* and *Nocardia.*

The "administration" of the vaccine according to the invention to a human or animal target can be performed using any feasible method and route. Typically, the optimal way of administration will be determined by the type of the vaccine applied, and the characteristics of the target and the bacterial disease that it is intended to protect against. Depending on whether the vaccine according to the invention is based on an O/W or on a W/O emulsion, different techniques of administration can be applied. For example, as an O/W emulsion vaccine the vaccine according to the invention can be administered by enteral or mucosal route, i.e. via eye drop, nose drop, oral, enteric, oro-nasal drop, spray. Other possibility is via a method of mass administration, such as via drinking water, coarse spray, atomisation, on-feed, etcetera.

Preferred way of administration for a method of vaccination according to the invention is by parenteral route.

"Parenteral" refers to administration through the skin, for example by intramuscular, intraperitoneal, intradermal, submucosal, or subcutaneous route.

It goes without saying that the optimal route of administration of a vaccine according to the invention will depend on the specifics of the vaccine that is used, and on the particular characteristics of the target. A skilled person is perfectly capable of selecting and optimising such route and method of administration.

The volume of a dose of the vaccine according to the invention, e.g. when administered by parenteral route, is a volume that is acceptable for the target human or animal, and can for instance be between about 0.01 and about 10 ml. Preferably one dose is a volume between 0.05 and 1 ml, more preferably one dose is between 0.1 and 0.5 ml.

When administered by intramuscular route, the volume of one dose is preferably between about 0.5 and about 3 ml, more preferably between 1 and 2 ml.

When administered by intradermal route, the volume of one dose is preferably between about 0.1 and about 0.5 ml, more preferably about 0.2 ml.

For fish vaccines, the volume of a dose of the vaccine according to the invention, e.g. when administered by parenteral route, is a volume that is acceptable for the target fish, and can for instance be between about 0.001 ml and about 5 ml. Preferably one dose is a volume between 0.01 ml and 2 ml, more preferably one dose is between 0.02 ml and 1 ml, more preferably between 0.05 ml and 0.5 ml.

When administered by intramuscular route, the volume of one dose is preferably between about 0.01 ml and about 3 ml, more preferably between 0.05 ml and 2 ml, more preferably between 0.1 ml and 0.5 ml.

The method, timing, and volume of the administration of a liquid vaccine composition according to the invention is preferably integrated into existing vaccination schedules of other vaccines that the target human or animal may require, in order to reduce stress to the target and to reduce labour costs. These other vaccines can be administered in a simultaneous, concurrent or sequential fashion, in a manner compatible with their registered use.

Therefore, in an embodiment, the vaccine according to the invention comprises at least one additional antigen.

The invention is directed to treating fish. The invention is directed to treating a disease caused by salmon alpha virus (SAV).

The invention is directed to a vaccine composition comprising an antigen from an intracellular pathogen, wherein the composition comprises less than 5% serum.

The invention is directed to a vaccine composition comprising an antigen from an intracellular pathogen, wherein the composition comprises less than 2.5 g/L of albumin.

The invention is further directed to a vaccine composition according to anyone of the embodiments as described herein wherein the intracellular pathogen is a virus, an intracellular bacterium, or an intracellular parasite.

The invention is further directed to a vaccine composition according to anyone of the embodiments as described herein wherein albumin is post translational modified albumin or native albumin.

The invention is further directed to a vaccine composition according to anyone of the embodiments as described herein wherein the antigen is from a fish pathogen, preferably an antigen of a salmon pathogen.

The invention is further directed to a vaccine composition according to anyone of the embodiments as described herein wherein the pathogen is a virus, preferably selected from the group comprising salmon alpha virus (SAV), Red Sea bream iridovirus (RSIV), Infectious Haematopoietic Necrosis virus (IHNV), viral Haemorrhagic Septicaemia virus (VHSV), Infectious Salmon Anaemia virus (ISAV), channel Catfish virus (CCV), Spring Viraemia of Carp virus (SVCV), Nervous Necrosis virus (NNV), Grass Carp haemorrhage disease virus (GCHDV), Tilapia Lake virus (TLV), marine aquabimavirus (MABV), Epizootic Hematopoietic Necrosis virus (EHNV), Piscine Reovirus (PRV), and Cardiomyopathy Virus (CMV).

The invention is further directed to a vaccine composition according to anyone of the embodiments as described herein wherein the pathogen is an intracellular bacterium, preferably selected from the group comprising *Piscirickettsia, Franciscella*, Chlamidia, *Rickettsia, Coxiella*.

The invention is further directed to a vaccine composition according to anyone of the embodiments as described herein wherein the pathogen is an intracellular parasite, preferably selected from the group comprising Apicomplexa and *Trypanosoma*.

The invention is further directed to a vaccine composition according to anyone of the embodiments as described herein wherein the pathogen is not Infectious Pancreatic Necrosis virus (IPNV).

The invention is further directed to a vaccine composition according to anyone of the embodiments as described herein wherein the pathogen is a killed, live or live attenuated intracellular pathogen.

The invention is further directed to a vaccine composition according to anyone of the embodiments as described herein wherein the pathogen has been grown on a cell-culture.

The invention is further directed to a vaccine composition according to anyone of the embodiments as described herein wherein the pathogen is a whole pathogen or derived from a whole pathogen.

The invention is further directed to a vaccine composition according to anyone of the embodiments as described herein wherein, the vaccine comprises less than 0.5 g/L of native albumin or post-translational modified albumin.

The invention is further directed to a vaccine composition according to anyone of the embodiments as described herein wherein, the vaccine comprises less than 0.5% of serum.

The invention is further directed to a vaccine composition according to anyone of the embodiments as described herein wherein the serum, the native albumin or the post-translational modified albumin is sourced from bovine, sheep, chicken, goat, horse, lamb, newborn calf, porcine, or rabbit.

The invention is further directed to a vaccine composition according to anyone of the embodiments as described herein, wherein the serum is fetal calf serum.

The invention is further directed to a vaccine composition according to anyone of the embodiments as described herein wherein the post-translational modification of albumin is selected from the group consisting of citrullination, carbamylation, glycation, cysteinylation, S-nitrosylation, S-transnitrosation and S-guanylation.

The invention is also directed to a vaccine according to any one of the embodiments described herein for use in method of treating a disease caused by the intracellular pathogen in an animal and reducing, preventing or avoiding cross-stitch spinal deformity in said animal.

The invention is also directed to method of treating or preventing a disease caused by the intracellular pathogen in an animal and reducing, preventing or avoiding cross-stitch spinal deformity in said animal, said method comprising the steps of administering to an animal in need a therapeutically effective amount of a vaccine according to any one of the embodiments described herein.

The invention is also directed to the use of a vaccine according to any one of the embodiments described herein in the manufacturing of medicine for treating a disease caused by the intracellular pathogen in an animal and reducing, preventing or avoiding cross-stitch spinal deformity in said animal.

The invention is directed to treating fish. The invention is directed to treating a disease caused by salmon alpha virus (SAV).

The invention will now be further described by the following, non-limiting, examples.

EXAMPLES

1. Example 1

Test were performed with different vaccines with different antigens. All vaccines were oil-emulsion vaccines.

TABLE 1

| | | | | |
|---|---|---|---|---|
| | | vaccines | | |
| Group | Vaccine | | Dose volume per fish (ml) | +/−serum/albumin |
| C1 | Inactivated SPDV (Salmon pancreas disease virus) ≥75% RPP Inactivated infectious pancreas necrosis virus (IPNV) serotype Sp ≥1,5 ELISA-units Inactivated *Aeromonas salmonicida* subsp. | | 0.1 | SPDV component contained serum |

TABLE 1-continued

| | | | |
|---|---|---|---|
| | vaccines | | |
| Group | Vaccine | Dose volume per fish (ml) | +/−serum/albumin |
| | *salmonicida* ≥10,7 log$_2$ ELISA-units, Inactivated *Vibrio salmonicida* ≥90 RPS, Inactivated *Vibrio anguillarum* serotype O1 ≥75 RPS, Inactivated *Vibrio anguillarum* serotype O2a ≥75 RPS, Inactivated Moritella viscosa ≥5,8 log$_2$ ELISA-units. Adjuvant; mineral oil | | |
| C2 | Inactivated infectious pancreas necrosis virus (IPNV) serotype Sp ≥1,5 ELISA-units Inactivated *Aeromonas salmonicida* subsp. *salmonicida* ≥10,7 log$_2$ ELISA-units, Inactivated *Vibrio salmonicida* ≥90 RPS, Inactivated *Vibrio anguillarum* serotype O1 ≥75 RPS, Inactivated *Vibrio anguillarum* serotype O2a ≥75 RPS, Inactivated Moritella viscosa ≥5,8 log$_2$ ELISA-units. Adjuvant; mineral oil | 0.1 | No serum |
| C3 | Inactivated SPDV (Salmon pancreas disease virus) ≥75% RPP Inactivated *Aeromonas salmonicida* subsp. *salmonicida* ≥10,7 log$_2$ ELISA-units, Inactivated *Vibrio salmonicida* ≥90 RPS, Inactivated *Vibrio anguillarum* serotype O1 ≥75 RPS, Inactivated *Vibrio anguillarum* serotype O2a ≥75 RPS, Inactivated Moritella viscosa ≥5,8 log$_2$ ELISA-units. Adjuvant; mineral oil | 0.1 | SPDV component contained serum around 6% |
| C4 | Inactivated SPDV (Salmon pancreas disease virus) ≥75% RPP Inactivated infectious pancreas necrosis virus (IPNV) serotype Sp ≥1,5 ELISA-units Inactivated *Aeromonas salmonicida* subsp. *salmonicida* ≥10,7 log$_2$ ELISA-units, Inactivated *Vibrio salmonicida* ≥90 RPS, Inactivated *Vibrio anguillarum* serotype O1 ≥75 RPS, Inactivated *Vibrio anguillarum* serotype O2a ≥75 RPS, Adjuvant; mineral oil | 0.1 | SPDV component contained serum around 6% |
| C5* | Inactivated *Aeromonas salmonicida* subsp. *Salmonicida* RPS ≥80, Inactivated *Listonella anguillarum* serotype O1 RPS ≥75, Inactivated *Listonella anguillarum* serotype O2a RPS ≥75, Inactivated *Vibrio salmonicida* RPS ≥90, Inactivated *Moritella viscosa* RPS ≥60, I Inactivated infectious pancreas necrosis virus (IPNV) serotype Sp 0,2 AU, Adjuvant: mineral oil Inactivated SPDV (Salmon pancreas disease virus), RPS ≥80% Adjuvant: mineral oil; Sorbitanoleat Polysorbat 80 | 0.05 + 0.05 | IPNV and SPDV component comprising serum |
| C6 | saline Sterile 0.9% NaCl in bottle | 0.1 | No serum |

*a 6-valent vaccine and a vaccine with PD was administered simultaneously
Serum comes from the culture process of The fish population was subjected to winter signal (12:12 light:dark period) 7 weeks prior to vaccination. Following smoltification (switch to 24:0 light:dark period) and an immunization period of minimum 500 degree days, the fish were transferred to sea. The fish were reared in sea until harvest about a year later.

The fish were individually PIT-tagged at least two weeks prior to vaccination. Fish samples were collected prior to sea transfer and at 4 time points during the ongrowing period in sea. X-ray analysis of the spine and bone strength measure- ments were performed on the samples. In addition, length and weight as well as classical local vaccine side effects were registered.

After transfer to sea (week 0) sampling is collected at week 7, 19, 31 and at harvest (approximately 14 months).

The experimental fish were from the same population and were reared under identical conditions until they randomly were assigned to the different vaccine groups (C1-C6). The vaccine groups were mixed and distributed equally when transferred to the sea cage units (70 fish from each vaccine group per sea cage). Identification of vaccine treatment groups were done by scanning and registration of the pre-implanted PIT-tag. The fish were anaesthetized before vaccination. The correct injection dose (see volumes in Table 1) were administered by intraperitoneal injection. The simultaneous injection of the 2×0.05 ml injection of C5, was done with an injector with Y-coupling.

FIG. 2 cross-stitch spinal deformities as determined by X-ray categorised by number of affected vertebrae. FIG. 2 shows that in the groups wherein the fish were vaccinated with vaccines without serum (C2 and C6) do not show cross-stitch spinal deformities or only very little. In contrast, all vaccine groups wherein a vaccine is used that contains serum or albumin show cross-stitch spinal deformities.

2. Example 2

Test were performed to see whether a function feed ingredient had any effect. Vaccines as indicated in table 1 were tested wherein the fish were given a fortified diet with beta glucan, see table 2. Experiments was carried out as described under example 1.

TABLE 2

| Main ingredients in diet: | |
| --- | --- |
| diett | % |
| Fish meal | 14.5 |
| Soya proteinconcentrate | 19 |
| weatgluten | 15 |
| weat | 7 |
| Hestebønner | 5 |
| Mais gluten | 5 |
| Fish oil | 10.5 |
| Rapeseed oil | 15 |
| Soyalechitin | 1 |
| Vitaminmix | 2 |
| Mineralmix | 0.59 |
| Mononatriumfosfat | 2.5 |
| Yttrium | 0.01 |
| Choline Chloride | 0.5 |
| Carop. Pink (10% Astax) | 0.05 |
| DL- Metionin | 0.8 |
| L-Lysin | 1.4 |
| Treonin | 0.2 |
| Sum | 100 |

3. Example 3 Elisa

Elisa experiments were performed of reactivity of sera from fish against adherent CHSE cell culture medium that is used to grow PD virus. The cell culture medium contains about 10% of fetal calf serum. Sera from fish from one farm were pooled and tested for reactivity against adherent CHSE cell culture medium. Fish were sampled and sera was collected.

Elisa plates were coated with CHSE cell culture medium in Elisa coating buffer overnight at 4° C. Plates were washed. Plates were blocked with 0.5% BSA (recombinant). Plates were washed and incubated (2 hours) with fish sera. Plates were washed and incubated (1 hour) with mouse IgG2a anti-salmon IgM. Plates were again washed and then incubated (1 hour) with goat HRP anti-mouse IgG. Plates were washed and developed with ABTS ELISA Peroxidase Substrate (2,2'-azino-bis(3-ethylbenzothiazoline-6-sulphonic acid) and measured.

FIG. 3 shows that sera from fish from farms where no spinal deformities were observed have a much lower reactivity against adherent CHSE cell culture medium. Whereas sera from fish from farms were spinal deformities was observed showed a significantly higher reactivity against adherent CHSE cell culture medium. One-way Anova, unpaired t-test and Welch's t-test showed all significant differences.

FIG. 4 shows Elisa results from the vaccination groups of experiment 1. Here it can be seen that sera from fish that were vaccinated with vaccines that comprised serum (C1 and C5) showed a significantly higher reactivity against adherent CHSE cell culture medium than sera from fish that were vaccinated with vaccines that did not comprise serum (C2 and C6).

4. Example 4 Western Blots

Samples: 5 ug/lane of either adherent CHSE culture medium or BSA (Bovine Serum Albumin Fraction V, 100 g; SIGMA ALDRICH CHEMIE B.V., cat No: 10735086001) were loaded in each lane of an SDS-PAGE gel. Samples were run for approximately 1 h and then transferred to a nitrocellulose membrane (Whatman protran nitrocellulose 0.45 um). 5 minutes wash in TBS-tween (TBS-T; 20 mM Tris-Cl, pH 7.5, 500 mM NaCl, 0.05% (v/v) Tween 20 (Sigma)) and then blocking for 1 h in 5% non-fat dry milk in TBS-T Serum from a pool of five fish were diluted 2000, 4000 or 6000 times in TBS-T and incubated for 2 h at room temperature. Serum was from either fish positive for spinal deformities or from fish negative for spinal deformities. Wash twice for 5 min in TBS-Tween/Triton (TBS-T+0.2% (v/v) Triton X-100; (Sigma))

Wash once for 5 min in TBS-T and incubate for 1 h with mouse IgG2a anti-salmon IgM (2 µg/mL, Immunoprecise). Wash twice for 5 min in TBS-TT, wash once for 5 min in TBS-T and incubate for 1 h with Goat anti-mouse IgG, Alexa-680 conjugated, (1:10000, Abcam) and then washed four times 5 min in TBS-TT. The western blots were imaged with the Odyssey image system, LI-COR.

FIG. 5 shows that sera from fish that are positive for SDS react strongly to cell culture medium but not or almost not to high grade bovine serum albumin. Sera from fish that are negative for SDS do not react or almost not react to cell culture medium and high grade bovine serum albumin.

The invention claimed is:
1. A method for administering a vaccine composition to fish comprising:
   administering to a fish in need thereof, a vaccine composition comprising:
      an antigen from an intracellular pathogen, and;
      less than 5% serum, wherein the less than 5% serum prevents or ameliorates in the fish the occurrence of a spinal deformity associated with the administration of the vaccine composition, wherein the spinal deformity is characterized by a complete collapse of the intervertebral space;
   wherein:
      the vaccine comprises less than 2.5 g/L of albumin,
      the antigen is a whole intracellular pathogen or an antigen obtained from a whole intracellular pathogen;
      the intracellular pathogen is a salmon pathogen; and
      the intracellular pathogen has been grown on cell culture.
2. The method of claim 1, wherein the albumin is post-translational modified albumin or native albumin.

3. The method of claim 2, wherein the vaccine composition comprises less than 0.5 g/L of native albumin or post-translational modified albumin.

4. The method of claim 2, wherein the post-translational modification of albumin is selected from the group consisting of citrullination, carbamylation, glycation, cysteinylation, S-nitrosylation, S-transnitrosation and Sguanylation.

5. The method of claim 1, wherein the intracellular pathogen is a virus, an intracellular bacterium, or an intracellular parasite.

6. The method of claim 1, wherein the pathogen is a virus selected from the group consisting of salmon alpha virus (SAV), Red Sea bream iridovirus (RSIV), Infectious Haematopoietic Necrosis virus (IHNV), viral Haemorrhagic Septicaemia virus (VHSV), Infectious Salmon Anaemia virus (ISAV), channel Catfish virus (CCV), Spring Viraemia of Carp virus (SVCV), Nervous Necrosis virus (NNV), Grass Carp haemorrhage disease virus (GCHDV), Tilapia Lake virus (TLV), marine aquabirnavirus (MABV), Epizootic Hematopoietic Necrosis virus (EHNV), Piscine Reovirus (PRV), Infectious Pancreatic Necrosis virus (IPNV) and Cardiomyopathy Virus (CMV).

7. The method of claim 1, wherein the pathogen is an intracellular bacterium selected from the group consisting of *Piscirickettsia*, *Franciscella*, Chlamidia, *Rickettsia*, *Coxiella*, *Aeromonas*, *Vibrio*, and Moritella.

8. The method of claim 1, wherein the intracellular pathogen is an intracellular parasite selected from the group consisting of Apicomplexa and *Trypanosoma*.

9. The method of claim 1, wherein the antigen is a killed, live, or live attenuated intracellular pathogen.

10. The method of claim 1, wherein the vaccine composition comprises less than 0.5% of serum.

11. The method of claim 1, wherein the serum is sourced from an animal selected from the group consisting of a bovine, a sheep, a chicken, a goat, a horse, a lamb, a newborn calf, a porcine, and a rabbit.

12. The method of claim 1, wherein the serum is fetal calf serum.

* * * * *